(12) United States Patent
Fujita

(10) Patent No.: US 8,737,568 B2
(45) Date of Patent: May 27, 2014

(54) METHOD OF REMOVING FOIL SHADOWS OF A SYNCHRONOUS GRID, AND A RADIOGRAPHIC APPARATUS USING THE SAME

(75) Inventor: Akinori Fujita, Osaka (JP)

(73) Assignee: Shimadzu Corporation, Kyoto (JP)

( * ) Notice: Subject to any disclaimer, the term of this patent is extended or adjusted under 35 U.S.C. 154(b) by 342 days.

(21) Appl. No.: 13/324,098

(22) Filed: Dec. 13, 2011

(65) Prior Publication Data

US 2012/0148022 A1  Jun. 14, 2012

(30) Foreign Application Priority Data

Dec. 13, 2010 (JP) ................. 2010-277193

(51) Int. Cl.
*G21K 1/10* (2006.01)

(52) U.S. Cl.
USPC ..................... 378/98.12; 378/154

(58) Field of Classification Search
CPC .... A61B 6/487; A61B 6/5252; A61B 6/5258; A61B 6/5282; A61B 6/4291; G06T 2207/10121
USPC ............... 378/98.12, 154, 155; 382/130, 132
See application file for complete search history.

(56) References Cited

U.S. PATENT DOCUMENTS

| 6,501,829 B2 | 12/2002 | Matsumoto et al. | |
| 8,233,659 B2 * | 7/2012 | Fujita | 382/100 |
| 8,284,902 B2 * | 10/2012 | Fujita | 378/155 |
| 8,559,754 B2 * | 10/2013 | Fujita | 382/275 |

FOREIGN PATENT DOCUMENTS

| JP | 2000-83951 A | 3/2000 |
| JP | 2002-257939 A | 9/2002 |
| JP | 2008-232731 A | 10/2008 |
| WO | 2010/134295 A1 | 11/2010 |

* cited by examiner

*Primary Examiner* — Glen Kao
(74) *Attorney, Agent, or Firm* — McDermott Will & Emery LLP

(57) ABSTRACT

An extracting step (step S1) extracts uninfluenced pixels with a relatively high degree of certainty, while avoiding influences of random quantum noise as much as possible. An approximate fluoroscopic image is obtained based on such uninfluenced pixels (step S2). Thus, accuracy of the approximate fluoroscopic image can be improved over that of the prior art. Therefore, a grid foil shadow image (step S3) and a foil shadow standard image (step S4) calculated successively based on the approximate fluoroscopic image have improved accuracy over the prior art. As a result, while inhibiting influences of random quantum noise, a foil shadow removed image can be obtained which is free from artifacts due to distortion of a synchronous grid.

20 Claims, 15 Drawing Sheets

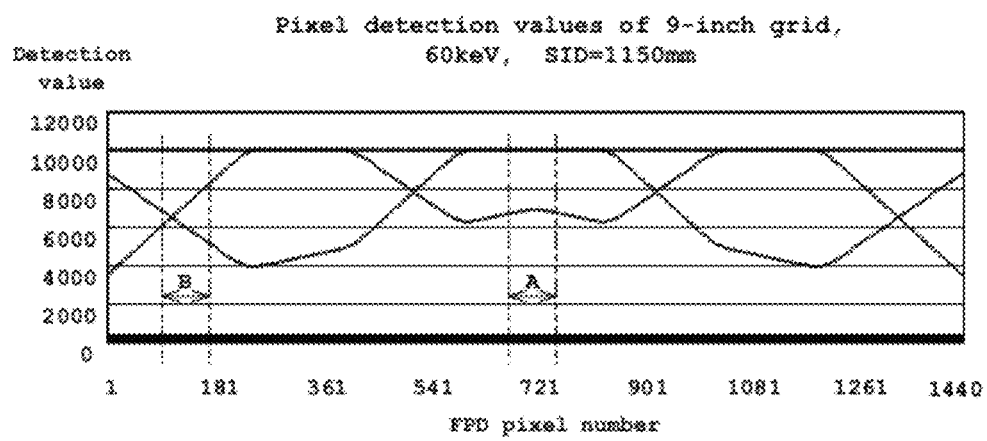
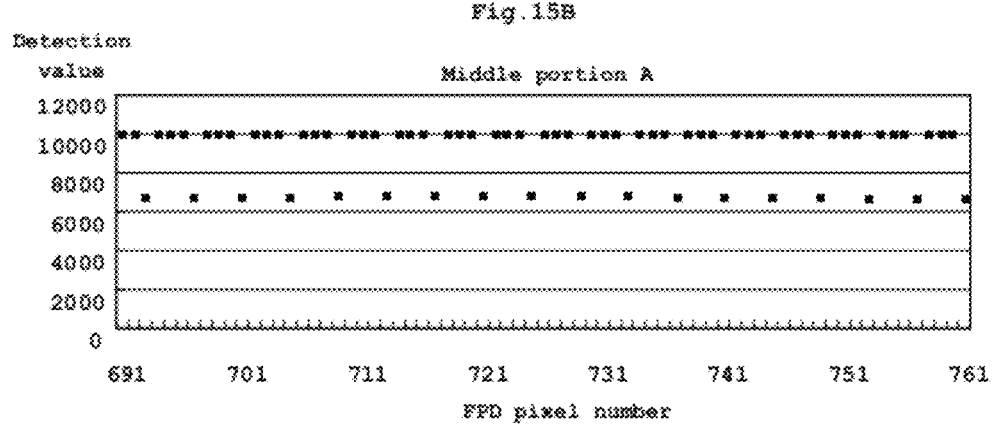
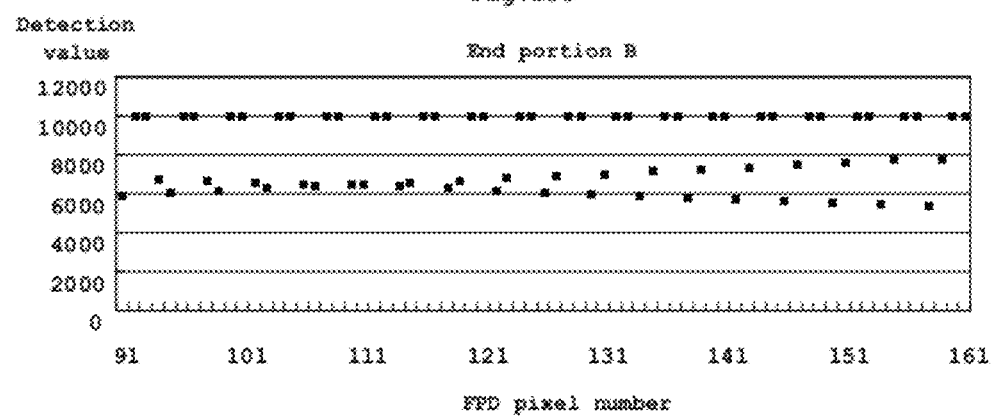

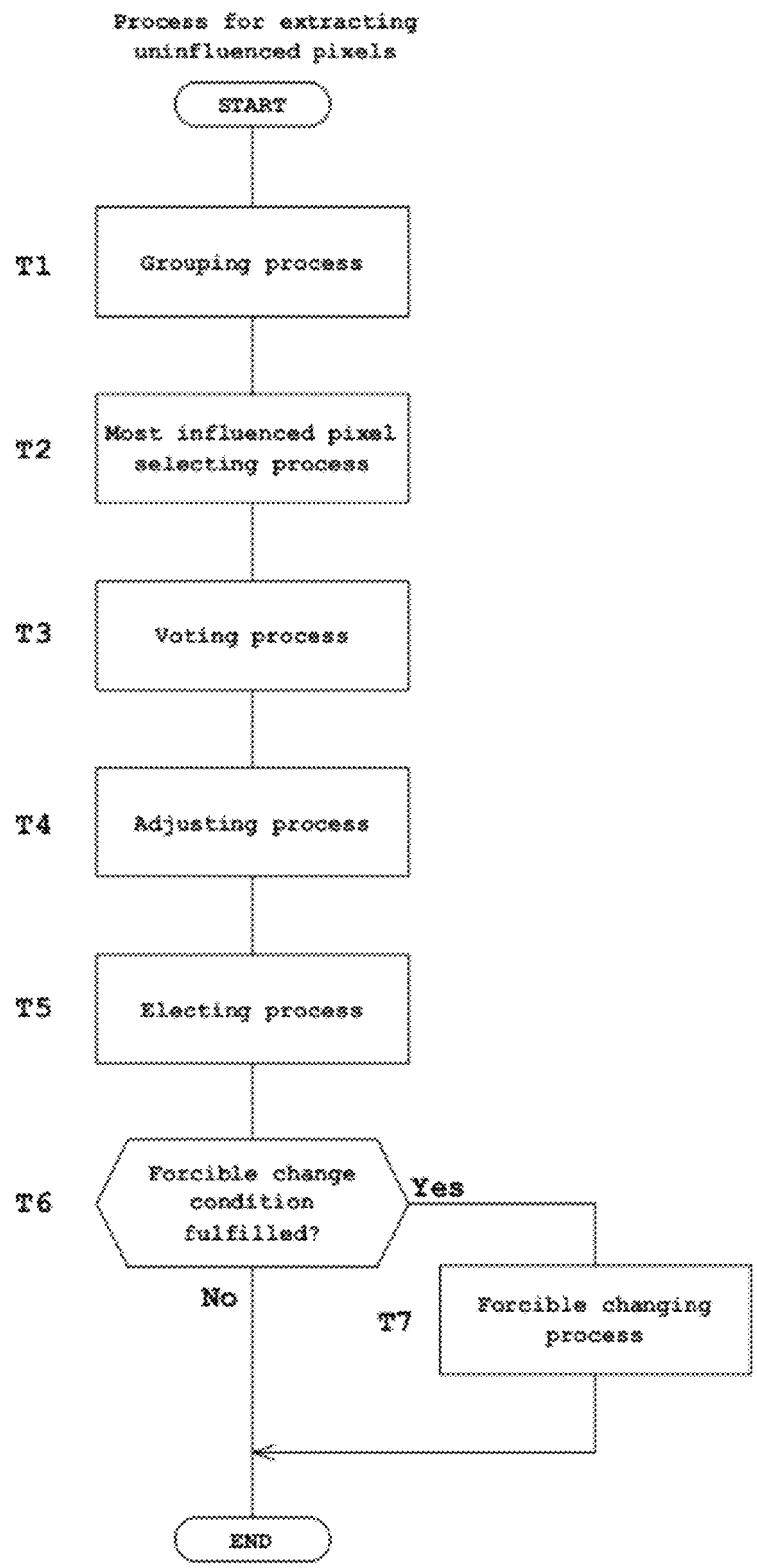

Inappropriate selection of uninfluenced pixels

After forcible change

Fig.20A
Invention
Fig.20B
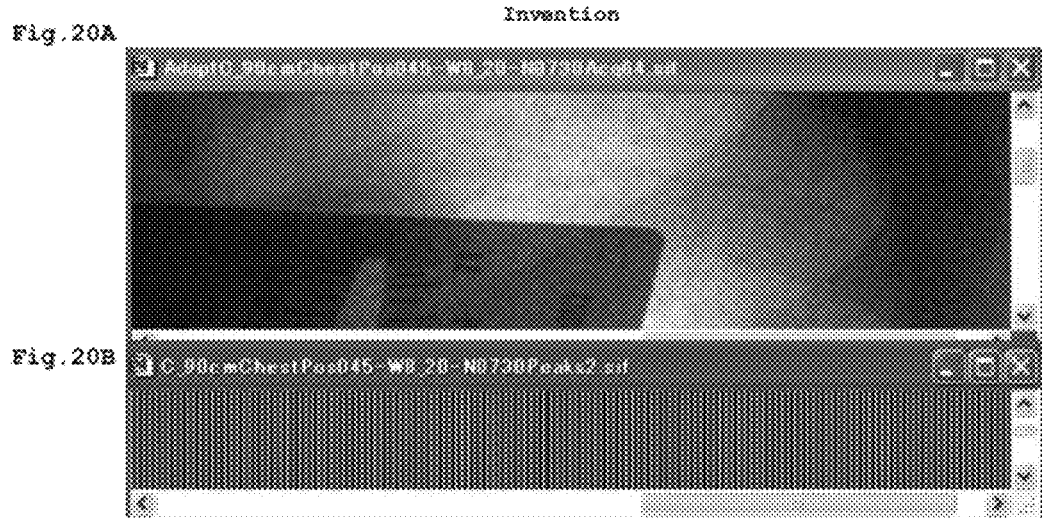
Fig.21A
Case of extracting uninfluenced pixels from maximum value of every four pixels
Fig.21B

METHOD OF REMOVING FOIL SHADOWS OF A SYNCHRONOUS GRID, AND A RADIOGRAPHIC APPARATUS USING THE SAME

CROSS-REFERENCE TO RELATED APPLICATIONS

The present application claims priority under 35 U.S.C. §119 to Japanese Patent Application No. 2010-277193, filed Dec. 13, 2010, which is incorporated herein by reference.

BACKGROUND OF THE INVENTION (1) Field of the Invention

This invention relates to a method of removing foil shadows of a synchronous grid which removes scattered radiation of a radiographic apparatus, and a radiographic apparatus using the same.

(2) Description of the Related Art

Conventionally, an X-ray apparatus includes an X-ray tube, and an X-ray detector opposed to the X-ray tube. The X-ray detector has a grid disposed adjacent an X-ray incident plane thereof. The grid reduces image quality degradation due to scattered X-rays, but on the other hand, grid foil shadows are superimposed on radiographic images.

An FPD (Flat Panel Detector) has come to be used widely as the X-ray detector in recent years. The FPD can improve the spatial resolution and X-ray sensitivity of radiographic images, and for this and other reasons its use is spreading at a rapid rate. However, as improvement is made in the spatial resolution and X-ray sensitivity of the X-ray detector, the grid foil shadows appear clearly on radiographic images, which are obstructive to interpretation of the radiographic images. In order to remove these grid foil shadows from the radiographic images, it is known to remove the shadows by image processing using frequency conversion. See Patent Document 1 (Japanese Unexamined Patent Publication No. 2000-83951 (paragraphs "0033"-"0036")), for example.

Patent Document 1 describes what is called a fixed grid which is fixedly attached to the X-ray detector although changeable to one different in grid intervals. Besides the above fixed grid, there is a moving grid. The moving grid is moved in a direction perpendicular to grid stripes synchronously with X-ray irradiation to prevent a fixed pattern of the grid from appearing on radiographic images. Although the fixed pattern of the grid does not appear on radiographic images, the moving grid has problems of requiring a complicated moving mechanism and lowering detection efficiency. Such grids are constructed of an alternate arrangement of metal foil strips consisting of an X-ray absorbing material such as lead, and interspacers consisting of aluminum or carbon fiber which does not easily absorb X-rays. However, these interspacers absorb a certain quantity of X-rays, which leads to a sensitivity lowering of desired X-ray images. So, a synchronous grid has been proposed as a solution to these problems. See Patent Document 2 (Japanese Unexamined Patent Publication No. 2002-257939 (paragraphs "0018" and "0019", and FIG. 1)).

This synchronous grid has grid foil strips arranged so that grid foil shadows fall in middles of detecting pixels of the FPD. More particularly, the grid foil strips are arranged as inclined such that each has flat surfaces thereof aligned to a straight line extending between a focus of the X-ray tube and an X-ray detecting plane of the FPD.

Patent Document 3 (Japanese Unexamined Patent Publication No. 2008-232731 (paragraphs "0001"-"0003" and "0007")), for example, describes a specific method of manufacturing a synchronous grid. This method excludes the interspacers members to provide layers of air, thereby to obtain X-ray images of improved sensitivity.

However, the conventional example with such construction has the following problems.

For reasons of manufacture of the grid foil strips and construction for aligning the grid foil strips, the synchronous grid has a certain distortion of the linear grid foil strips and a minute shift in their positions of arrangement. Further, since the grid foil strips of the synchronous grid are higher than those of the other type grids, the foil shadows of the synchronous grid are susceptible to influences of the distortion and shifting of the grid foil strips. Distortion and shifting occur also with the grid foil shadows, which are caused by the distortion and shifting of the grid foil strips. As a result, variations in measurements of the foil shadows will occur to different lines of the grid foil shadows, and density variations will occur to the grid foil shadows. There is a drawback that, even if frequency conversion is used for removing the grid foil shadows, the grid foil shadows in a longitudinal pattern cannot fully be removed. The grid foil shadows failing to be removed will become artifacts on radiographic images after the grid foil shadows are removed therefrom.

In an X-ray apparatus having a C-arm, the heavy X-ray tube and FPD are mounted at opposite ends of the C-arm. Thus, subtle bending of the C-arm will occur with movement such as rotation of the C-arm, thereby causing a shift between the FPD and the focus of the X-ray tube. This shift is in the order of 2 mm, for example, but the grid foil shadows on the FPD will also move, and hence a problem that the grid foil shadows cannot fully be removed.

In order to solve the above problems, Applicant has proposed the following technique (International Application PCT/JP2010/003221).

According to this technique, pixels free from influences of grid foil shadows are first extracted from a fluoroscopic image, and an interpolation process is carried out based on detection signal values of these pixels, to obtain an approximate fluoroscopic image without influences of the grid foil shadows. Next, a grid foil shadow image which is an image of only the grid foil shadows is obtained based on a difference between the fluoroscopic image and the approximate fluoroscopic image. Further, the grid foil shadow image is averaged to obtain a foil shadow standard image inhibiting variations in the grid foil shadows due to random errors such as quantum noise. Then, based on the foil shadow standard image and the fluoroscopic image, the grid foil shadows are removed from the fluoroscopic image. This is a technique intended to obtain, through such processes, a fluoroscopic image with no grid foil shadows appearing thereon.

It is important for the above proposed technique how the pixels free from influences of the grid foil shadows should be extracted. However, under the influence of random quantum noise occurring with X-rays, pixels influenced by the grid foil shadows can be extracted in error. Then, since the approximate fluoroscopic image has low accuracy, accuracy of the grid foil shadow image also becomes low. There arises a problem that it is impossible to remove the grid foil shadows from the fluoroscopic image ultimately with high accuracy, with artifacts remaining to impart influence.

SUMMARY OF THE INVENTION

This invention has been made having regard to the state of the art noted above, and its object is to provide a method of removing foil shadows of a synchronous grid and a radiographic apparatus using the same, which are capable of removing artifacts due to distortion of the synchronous grid while inhibiting adverse influences of random quantum noise.

The above object is fulfilled, according to this invention, by a grid foil shadow removing method for a radiographic apparatus for obtaining fluoroscopic images and having a synchronous grid with grid foil strips arranged at regular intervals so that grid foil shadows fall on middles of pixels which detect radiation, the method comprising an extracting step including a grouping step for dividing pixels forming a fluoroscopic image into groups each having a predetermined number of pixels within each row in a direction of row, a most influenced pixel selecting step for selecting a pixel most influenced by one of the grid foil shadows in each group as most influenced pixel, a voting step for casting, with the most influenced pixel in each group serving as a reference, a predetermined number of votes for other pixels spaced apart forward and backward in the direction of row, and an electing step for electing a pixel given a maximum number of votes within each group as an uninfluenced pixel which is free from influences of a foil shadow of the grid; an approximate fluoroscopic image calculating step for obtaining an approximate fluoroscopic image by carrying out an interpolation process based on detection signal values of the uninfluenced pixels; a grid foil shadow image calculating step for obtaining a grid foil shadow image based on a difference between the fluoroscopic image and the approximate fluoroscopic image; a foil shadow standard image calculating step for obtaining a foil shadow standard image by averaging the grid foil shadow image in a longitudinal direction of the grid foil shadows; and a foil shadow removing step for removing the grid foil shadows from the fluoroscopic image based on a difference between the fluoroscopic image and the foil shadow standard image, thereby to obtain a foil shadow removed image.

According to this invention, the pixels arranged in the direction of row are grouped in the grouping step, and the most influenced pixel within each group is selected in the most influenced pixel selecting step. The most influenced pixel is a pixel most influenced by a grid foil shadow, which can be selected relatively easily and relatively reliably compared with selection of pixels not influenced by the grid foil shadows. Next, in the voting step, votes are cast for other pixels spaced forward and backward in the direction of row from the most influenced pixel in each group, and in the electing step, a pixel given a maximum number of votes within each group is elected as an uninfluenced pixel which is free from influences of a grid foil shadow. By executing the extracting step including the above steps, pixels not influenced by the grid foil shadows can be extracted with a relatively high degree of certainty from among pixels with varied detection signal values due to random quantum noise of the radiation.

Then, in the approximate fluoroscopic image calculating step, an interpolating process is carried out based on the detection signal values of the uninfluenced pixels, to calculate an approximate fluoroscopic image with the grid foil shadows substantially removed from the fluoroscopic image. Further, the grid foil shadow image calculating step calculates a grid foil shadow image as an image of only the grid foil shadows based on a difference between the fluoroscopic image and the approximate fluoroscopic image. Since this grid foil shadow image has nonuniformity of the grid foil shadows due to influences of the random errors due to quantum noise and the like, the foil shadow standard image calculating step calculates a grid foil shadow standard image without influences of distortions due to noise, for example, by averaging the grid foil shadow image piecewise by units of several tens of pixels in the longitudinal direction. This averaging also can remove some errors in interpolating process. Next, the foil shadow removing step is executed to obtain a foil shadow removed image excluding the grid foil shadows from the fluoroscopic image based on a difference between the fluoroscopic image and the foil shadow standard image. As described above, the extracting step extracts uninfluenced pixels with a relatively high degree of certainty, while avoiding influences of random quantum noise as much as possible. An approximate fluoroscopic image is obtained based on such uninfluenced pixels. Thus, accuracy of the approximate fluoroscopic image can be improved over that of the prior art. Therefore, the grid foil shadow image and foil shadow standard image calculated successively based on the approximate fluoroscopic image have improved accuracy over the prior art. As a result, while inhibiting influence of random quantum noise, the foil shadow removed image is made free from artifacts due to distortion of the synchronous grid.

In this invention, it is preferred that, when the predetermined number of pixels constituting each group is four, and the predetermined number of votes is 1; the voting step casts 1 vote for each of a pixel located next but one forward and a pixel located next but one backward in the direction of row; and the electing step elects a pixel having obtained 2 votes as the uninfluenced pixel; the voting step and the electing step having, interposed therebetween, adjusting steps including a first adjusting step for adjusting the number of votes obtained to 2 for a pixel whose number of votes obtained is 1 when pixels located next but three to such pixel forward and backward in the direction of row have 2 votes, respectively; a second adjusting step for adjusting the number of votes obtained to 0 for a pixel whose number of votes obtained is 1 when a pixel located next to such pixel in the direction of row has 2 votes; a third adjusting step for comparing detection signal values of a pixel whose number of votes obtained is 1 and an adjoining pixel, adjusting the number of votes from 1 to 2 for the pixel having the larger detection signal value, and adjusting the number of votes to 0 for the pixel having the smaller detection signal value; and a fourth adjusting step for adjusting the number of votes obtained from 1 to 0 for a pixel whose number of votes obtained is 1 when one of pixels located next but one to such pixel forward and backward in the direction of row has 2 votes.

When the number of pixels constituting each group is four and the number of votes is 1, the voting step first casts 1 vote for each of a pixel located next but one forward and a pixel located next but one backward in the direction of row. Then, the electing step elects a pixel having obtained 2 votes at this point of time as the uninfluenced pixel. Further, at this point of time, there exist pixels with the number of votes obtained=1, for which it is unknown whether they are influenced by the foil shadows or not. Then, the adjusting steps including the first to fourth adjusting steps are executed for all pixels whose number of votes obtained is 1. First, the first adjusting step adjusts the number of votes obtained from 1 to 2 for a pixel when pixels located next but three to this pixel forward and backward in the direction of row have 2 votes, respectively. This is because, when four pixels form each group, a pixel next but three to a pixel having 2 votes has a high probability of not being influenced by a foil shadow. Next, the second adjusting step adjusts the number of votes obtained from 1 to 0 for a pixel when a pixel located next to this pixel in the direction of row has 2 votes. This is because the probability of two adjoining pixels not being influenced by a foil shadow or shadows is low. Next, the third adjusting step compares detection signal values of adjoining pixels, adjusts the number of votes to 2 for the pixel having the larger detection signal value, and adjusts the number of votes to 0 for the pixel having the smaller detection signal value. This is because, where pixels with 1 vote adjoin each other, the pixel with the larger detection signal value is more likely not to be influenced by a foil shadow. Next, the fourth adjusting step adjusts the number of votes obtained to 0 for a pixel when one of pixels located forward and backward next but one to this pixel has 2 votes. This is because, when a pixel not influenced by a foil shadow is present close by, the pixel in question has a high probability of being influenced by the foil shadow. These adjusting steps adjust many pixels with the number of votes 1 to have the number of votes=0 or the number of votes=2, which enables uninfluenced pixels to be extracted within the respective groups.

In this invention, it is preferred that the method further comprises a fifth adjusting step executed, when there remains a pixel whose number of votes obtained is 1 after the fourth adjusting step, for adjusting the number of votes obtained by such pixel to 2.

For a group located in an end portion, the votes are cast only from the group at one side, and there exists a pixel with the number of votes 1 remaining unchanged. So, this remaining pixel is adjusted to have 2 votes. This enables an uninfluenced pixel to be extracted from the end portion for use in the interpolation process. Therefore, the interpolation process for end portions can also be carried out with high accuracy.

In this invention, it is preferred that the method comprises a forcible changing step executed after the extracting step, when a predetermined range includes an uninfluenced pixel skipping four pixels, and an uninfluenced pixel skipping two pixels, for forcibly changing the uninfluenced pixels so that each have three pixels at both sides.

Even though uninfluenced pixels are extracted through the adjusting steps, there is a possibility of erroneous extraction since, after all, pixels only with a stochastically high degree of certainty are extracted. So, the forcible changing step assumes a high probability of erroneous extraction when a predetermined range includes an uninfluenced pixel skipping four pixels and an uninfluenced pixel skipping two pixels. Then, the uninfluenced pixels are forcibly changed so that each have three pixels at both sides. This can inhibit lowering of the accuracy of an approximate fluoroscopic image due to the erroneous extraction.

In another aspect of the invention, a radiographic apparatus for obtaining radiographs comprises a radiation emitting device for emitting radiation to a patient; a radiation detector having pixels arranged in a two-dimensional array for detecting radiation transmitted through the patient; a synchronous grid with foil strips arranged at regular intervals so that grid foil shadows fall on middles of the pixels of the radiation detector; an extracting unit including a grouping unit for dividing pixels forming a fluoroscopic image into groups each having a predetermined number of pixels within each row in a direction of row, a most influenced pixel selecting unit for selecting a pixel most influenced by one of the grid foil shadows in each group as most influenced pixel, a voting unit for casting, with the most influenced pixel in each group serving as a reference, a predetermined number of votes for other pixels spaced apart forward and backward in the direction of row, and an electing unit for electing a pixel given a maximum number of votes within each group as an uninfluenced pixel which is free from influences of a foil shadow of the grid; an approximate fluoroscopic image calculating unit for obtaining an approximate fluoroscopic image by carrying out an interpolation process based on detection signal values of the uninfluenced pixels; a grid foil shadow image calculating unit for obtaining a grid foil shadow image based on a difference between the fluoroscopic image and the approximate fluoroscopic image; a foil shadow standard image calculating unit for obtaining a foil shadow standard image by averaging the grid foil shadow image in a longitudinal direction of the grid foil shadows; and a foil shadow removing unit for removing the grid foil shadows from the fluoroscopic image based on a difference between the fluoroscopic image and the foil shadow standard image, thereby to obtain a foil shadow removed image.

According to this invention, the radiation emitting device emits radiation to a patient, and the radiation detector detects radiation transmitted through the patient. The resulting fluoroscopic image has grid foil shadows of the synchronous grid appearing thereon.

So, the grouping unit divides the pixels arranged in the direction of row into groups, and the most influenced pixel selecting unit selects the most influenced pixel within each group. The most influenced pixel is a pixel most influenced by a grid foil shadow, which can be selected relatively easily and relatively reliably compared with selection of pixels not influenced by the grid foil shadows. Next, the voting unit casts votes for other pixels spaced forward and backward in the direction of row from the most influenced pixel in each group, and the electing unit elects a pixel given a maximum number of votes within each group as an uninfluenced pixel which is free from influences of a grid foil shadow. With the extracting unit carrying out such processes, pixels not influenced by the grid foil shadows can be extracted with a relatively high degree of certainty from among pixels with varied detection signal values due to random quantum noise of the radiation.

Then, the approximate fluoroscopic image calculating unit carries out an interpolating process based on the detection signal values of the uninfluenced pixels, to calculate an approximate fluoroscopic image with the grid foil shadows substantially removed from the fluoroscopic image. Further, the grid foil shadow image calculating unit calculates a grid foil shadow image as an image of only the grid foil shadows based on a difference between the fluoroscopic image and the approximate fluoroscopic image. Since this grid foil shadow image has nonuniformity of the grid foil shadows due to the random errors due to quantum noise and the like, the foil shadow standard image calculating unit calculates a grid foil shadow standard image without influences of distortions, for example, by averaging the grid foil shadow image piecewise by units of several tens of pixels in the longitudinal direction. Next, the foil shadow removing unit obtains a foil shadow removed image excluding the grid foil shadows from the fluoroscopic image based on a difference between the fluoroscopic image and the foil shadow standard image. As described above, the extracting unit extracts uninfluenced pixels with a relatively high degree of certainty, while avoiding influences of random quantum noise as much as possible. An approximate fluoroscopic image is obtained based on such uninfluenced pixels. Thus, accuracy of the approximate fluoroscopic image can be improved over that of the prior art. Therefore, the grid foil shadow image and foil shadow standard image calculated successively based on the approximate fluoroscopic image have improved accuracy over the prior art. As a result, while inhibiting influence of random quantum noise, the foil shadow removed image is made free from artifacts due to distortion of the synchronous grid.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIG. 15 shows an example of detection values of the pixels within one row of the FPD, in which FIG. 15A shows detection values of the entire row, FIG. 15B shows detection values of a middle portion A, and FIG. 15C shows detection values of an end portion B;

FIG. 18 is a flow chart showing a process of extracting uninfluenced pixels;

FIG. 19 includes schematic views showing uninfluenced pixels after the extracting process, in which

FIG. 20 includes views showing a process according to this invention, in which FIG. 20A shows a foil shadow removed image, and FIG. 20B shows selected uninfluenced pixels; and FIG. 21 includes views showing a process according to a proposed example, in which FIG. 21A shows a foil shadow removed image, and FIG. 21B shows selected uninfluenced pixels.

DESCRIPTION OF THE PREFERRED EMBODIMENTS

Figure 1:
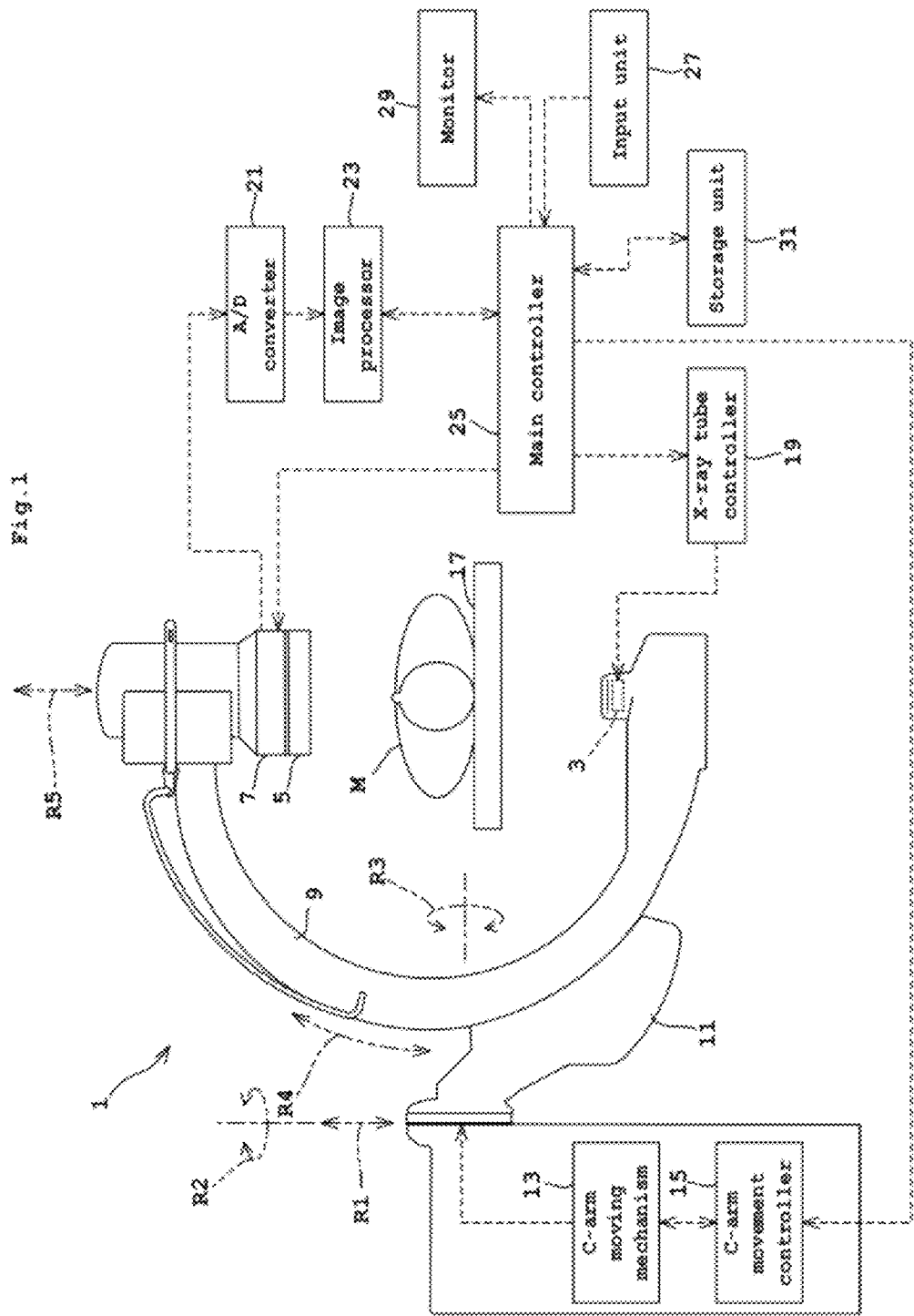
FIG. 1 is an overall view showing an outline of an X-ray fluoroscopic apparatus according to this invention.
Figure 2:
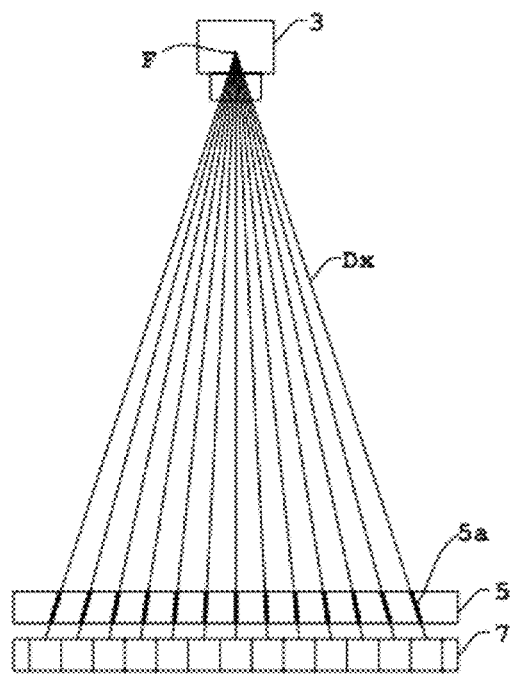
FIG. 2 is a view in vertical section of a grid.
Figure 3:
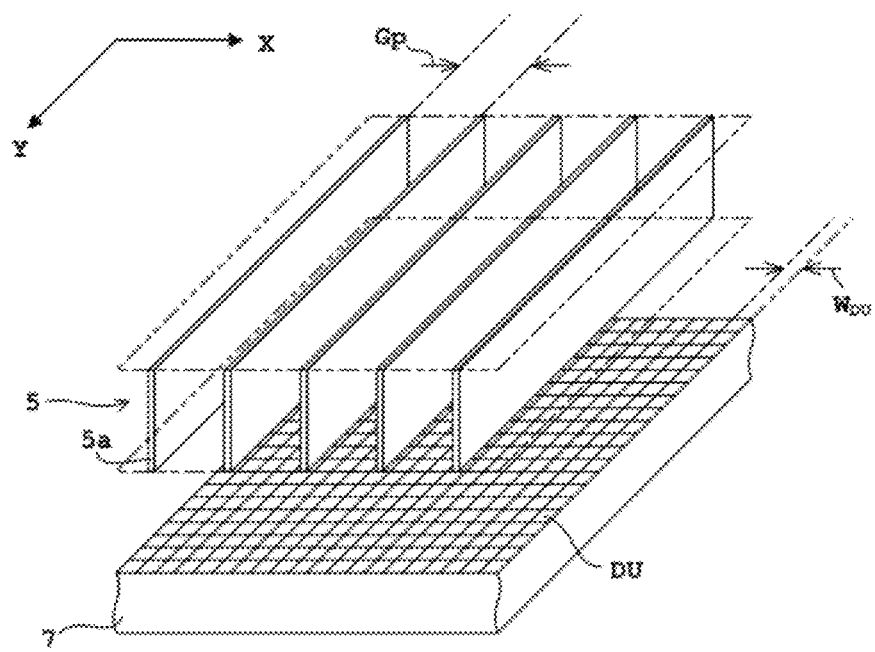
FIG. 3 is a perspective view of grid foil strips.

An embodiment of this invention will be described hereinafter with reference to the drawings. In this embodiment, an X-ray fluoroscopic apparatus will be described as an example of radiographic apparatus. FIG. 1 is an overall view showing an outline of an X-ray fluoroscopic apparatus according to the embodiment. FIG. 2 is a view in vertical section of a grid. FIG. 3 is a perspective view of grid foil strips.

An X-ray fluoroscopic apparatus 1 includes an X-ray tube 3, a synchronous grid 5 and a flat panel detector 7 (hereinafter called FPD). The X-ray tube 3 emits X-rays to a patient M. The synchronous grid 5 is attached to an X-ray incident side of the FPD 7 for removing scattered X-rays. The FPD 7 detects transmission X-rays emitted from the X-ray tube 3. The X-ray tube 3 and the synchronous grid 5/FPD 7 are mounted at opposite ends of a C-arm 9 to be opposed to each other. The C-arm 9 is supported by an arm support 11, and is moved by a C-arm moving mechanism 13. The C-arm moving mechanism 13 is controlled by a C-arm movement controller 15.

The above X-ray tube 3 corresponds to the "radiation emitting device" in this invention. The FPD 7 corresponds to the "radiation detecting device" in this invention.

The C-arm 9 is constructed movable up and down in vertical directions R1 relative to a top board 17 on which the patient M is placed. The arm support 11 is constructed rotatable about an axis R2 extending vertically. The C-arm 9 is also rotatable about a horizontal axis R3 and movable in arcuate rocking directions R4 relative to the arm support 11. In order to adjust an SID (Source Image Distance) which is a distance between the X-ray tube 3 and FPD 7, the synchronous grid 5 and FPD 7 are movable in vertical directions R5 by the C-arm moving mechanism 13.

The X-ray fluoroscopic apparatus 1 further includes an X-ray tube controller 19, an analog-to-digital converter 21, an image processor 23, a main controller 25, an input unit 27, a monitor 29 and a storage unit 31.

The X-ray tube controller 19 controls a tube current and tube voltage outputted to the X-ray tube 3. The analog-to-digital converter 21 converts X-ray detection signals outputted from the FPD 7, from analog to digital. The image processor 23 carries out various image processes on the digital X-ray detection signals. The main controller 25 has a CPU and so on for performing overall control of the X-ray tube controller 19 and other components. The input unit 27 has input devices such as a mouse used by the radiographer in making varied settings. The monitor 29 is used to give various displays such as control screens for X-ray diagnosis and X-ray fluoroscopic images picked up. The storage unit 31 is formed of a storage device such as hard disk or semiconductor memory for storing the X-ray fluoroscopic images and various data.

The synchronous grid 5 will be described with reference to FIGS. 2 and 3. The synchronous grid 5 is disposed to cover an X-ray detecting plane of the FPD 7. The synchronous grid 5 has grid foil strips 5a stretched to extend in a longitudinal (Y) direction. The grid foil strips 5a are formed of a material for absorbing X-rays. The grid foil strips 5a are arranged as inclined such that each has a flat surface thereof aligned to a straight line extending between a focus F of the X-ray tube 3 and the X-ray detecting plane of the FPD 7. In other words, the synchronous grid 5 has the grid foil strips 5a arranged so that grid foil shadows (hereinafter called simply foil shadows) may fall on middles of X-ray detecting pixels DU of the FPD 7.

Figure 4:
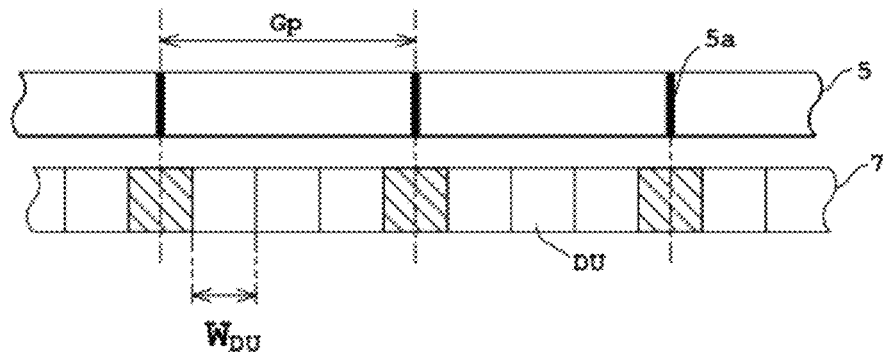
FIG. 4 is a view in vertical section showing a relationship between the grid and an FPD.

The grid foil strips 5a will be described with reference to FIGS. 3 and 4. FIG. 4 is a view in vertical section showing a relationship between the grid and FPD.

The grid foil strips 5a are arranged at predetermined intervals in a transverse (X) direction. The arrangement pitch Gp is 400 μm, for example. This arrangement pitch Gp is designed as appropriate to synchronize with the width $W_{DU}$ of the X-ray detecting pixels DU of the FPD 7. That is, the grid foil strips 5a are arranged so that, in a C-arm standard position at a reference SID, the foil shadows thereof may fall at predetermined pixel intervals on the X-ray detecting pixels DU. Since the width $W_{DU}$ of the X-ray detecting pixels DU is 100 μm in this embodiment, for example, the foil shadows will be cast in a ratio of one to four of the X-ray detecting pixels DU in the transverse direction.

The above grid foil strips 5a are formed of a simple substance such as molybdenum, tungsten, lead or tantalum, or an alloy having one or more of these as main component. These metals, preferably, are materials having large atomic numbers and high X-ray absorptivity. The grid foil strips 5a usually have a thickness of 20-50 μm. The grid foil strips 5a are manufactured by rolling, cutting and so on, but because of being a heavy metal or an alloy thereof, it is very difficult to secure uniformity in shapes such as in the thickness and width of the grid foil strips 5a. This shape nonuniformity of the grid foil strips 5a is a cause of the foil shadows producing variations in detection values.

The FPD 7 has X-ray detecting pixels DU arranged in a two-dimensional array for converting X-rays into charge signals. Specifically, for example, 1440×1440 X-ray detecting pixels DU are arranged.

The SID will be described now. The SID is a perpendicular distance between the focus of an X-ray source in the X-ray tube 3 and the FPD 7. When the SID is shortened, an enlarged fluoroscopic image of the patient M can be obtained. On the other hand, when the SID is elongated, a wide-field fluoroscopic image of the patient M can be obtained. That is, a zoom adjustment of fluoroscopic images can be made by adjusting the SID. It is assumed in this embodiment that the SID at 1000 mm is set as "reference SID". The grid foil strips 5a and FPD 7 are positionally adjusted to have one foil shadow falling on every four X-ray detecting pixels DU in the transverse direction of the FPD 7 when in the C-arm standard position at the reference SID. This is because, in the C-arm standard position, the C-arm 9 is considered free from bending due to its rigidity. The C-arm standard position is a position in which, as shown in FIG. 1, the C-arm 9 is in a positional relationship set three-dimensionally relative to the top board 17 or an examination room, and to which the C-arm 9 is initialized for every examination.

Figure 5:
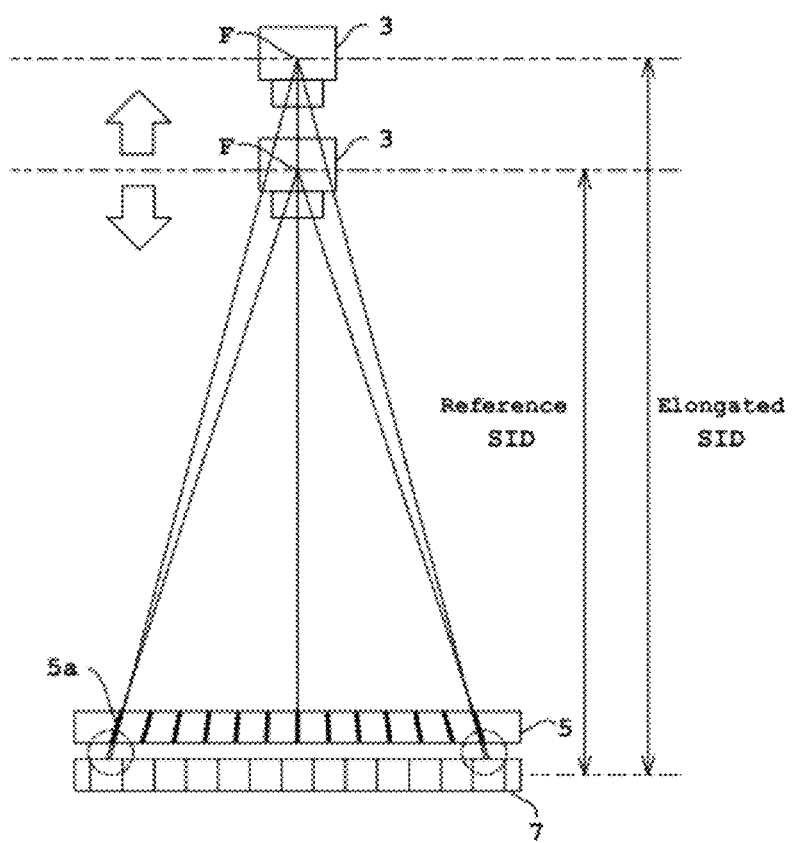
FIG. 5 is an explanatory view of SIDS.

Reference is now made to FIG. 5. FIG. 5 is an explanatory view of SIDs.

When the SID is changed, the foil shadows on the X-ray detecting plane will move. At an elongated SID which is longer than the reference SID, for example, although the foil shadows on a middle portion of the FPD 7 are little influenced, the foil shadows away from the middle portion toward side ends of the FPD 7 move inward of the FPD 7. Conversely, when the SID is made shorter than the reference SID, the foil shadows move outward of the FPD 7.

Figure 6:
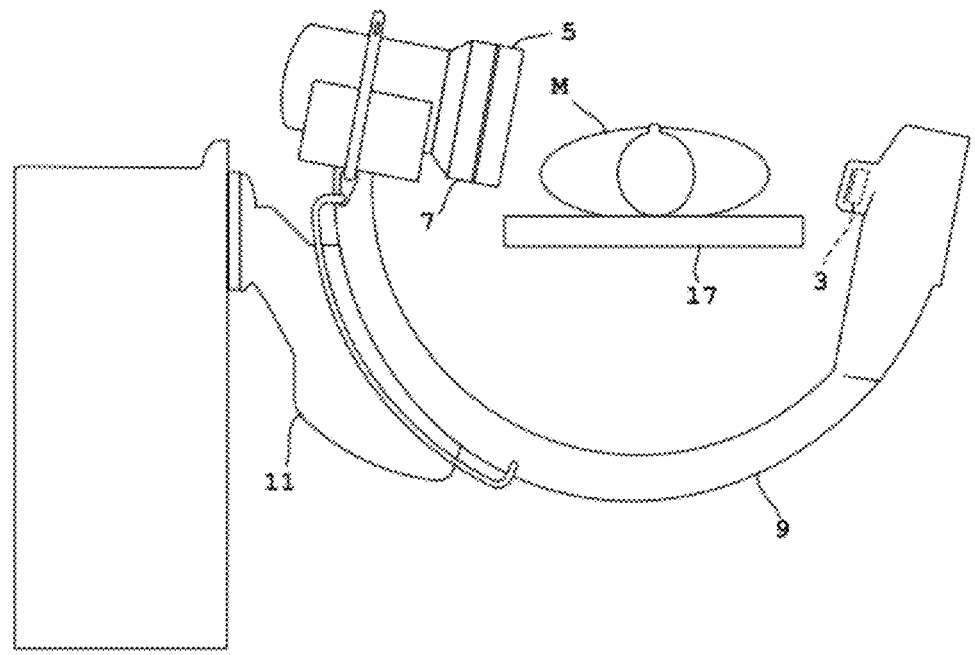
FIG. 6 is a view showing a C-arm having been moved.
Figure 7:
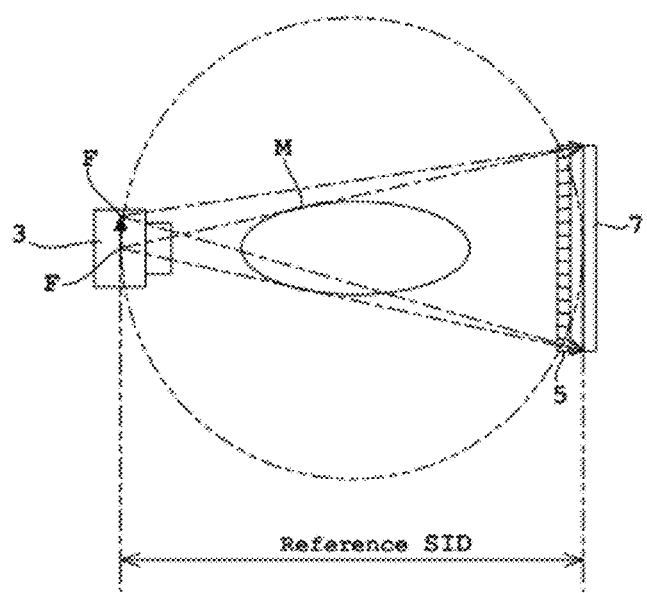
FIG. 7 is a schematic view illustrating movement of an X-ray focus.
Figure 8:
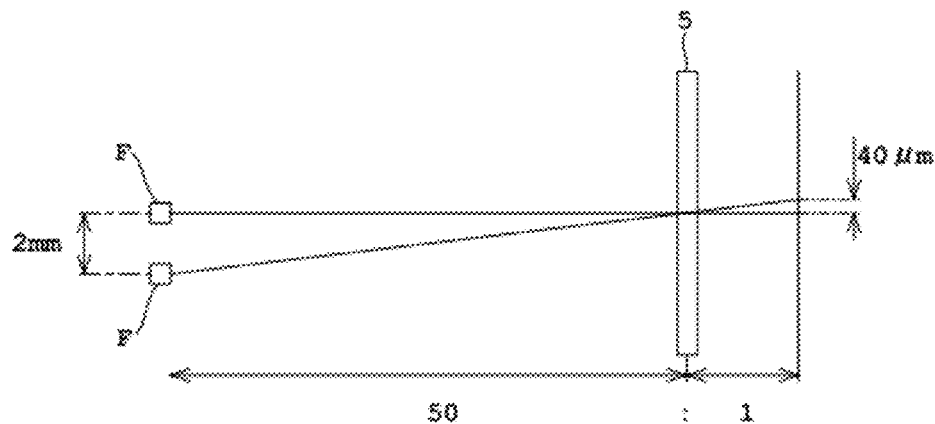
FIG. 8 is a schematic view illustrating movement of the X-ray focus.
Figure 9:
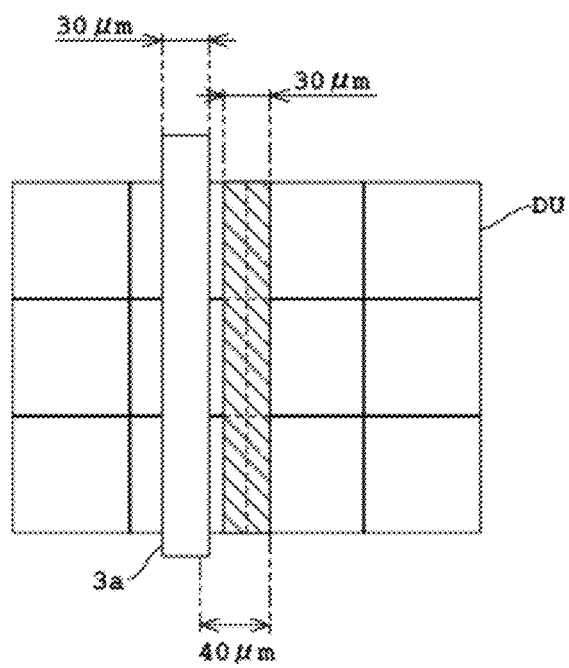
FIG. 9 is a schematic view illustrating movement of a grid foil shadow on pixels of the FPD.

The above movements of the foil shadows will occur also when the C-arm 9 is rotated, for example. Here, reference is made to FIGS. 6 through 9. FIG. 6 is a view showing the C-arm having been moved. FIGS. 7 and 8 are schematic views illustrating movement of the X-ray focus. FIG. 9 is a schematic view illustrating movement of a foil shadow on pixels of the FPD.

When the C-arm 9 is rotated to assume a position as shown in FIG. 6, a "bending" will occur to the C-arm 9 due to its rigidity. Then, the X-ray focus in the X-ray tube 3 will also move with this bending, and therefore the foil shadows will move, though minutely, also at the reference SID. This movement is, for example, about 2 mm at most. When the X-ray focus F in the X-ray tube 3 moves minutely as shown in FIG. 7, for example, the straight lines extending between the X-ray focus F and the detecting plane of the FPD 7 will become misaligned with the inclination angles of the flat surfaces of the grid foil strips 5a. Consequently, the foil shadows will move minutely on the X-ray detecting plane. As shown in FIG. 8, when the reference SID is 1000 mm and the distance between the synchronous grid 5 and the FPD 7 is 20 mm, the ratio between the distance from the focus F of the X-ray tube 3 to the synchronous grid 5 and the distance from the synchronous grid 5 to the FPD 7 is about 50:1. Therefore, when the focus F of the X-ray tube 3 moves 2 mm, the foil shadows of the grid foil strips 5a will move about 40 μm on the detecting plane of the FPD 7.

Assume that the thickness of the grid foil strips 5a is 30 μm and the width of the foil shadows also 30 μm, since a setting is made such that the foil shadows are located at the middles of the pixels when at the reference SID, there is an allowance of 35 μm from the foil shadows to adjoining pixels. On the other hand, when the above movement of the focus F of the X-ray tube 3 moves the foil shadows 40 μm, the foil shadows will, as shown in FIG. 9, protrude into the adjoining pixels from the pixels arranged beforehand to have the foil shadows cast thereon.

When an approximate fluoroscopic image is obtained by fixing pixels not influenced by the grid foil shadows, the accuracy of the approximate fluoroscopic image lowers due to such a phenomenon occurring to the foil shadow. This gives rise to a problem of lowering the accuracy of a fluoroscopic image with no grid foil shadows appearing thereon. It is characteristic of this invention to inhibit such an adverse influence.

Figure 10:
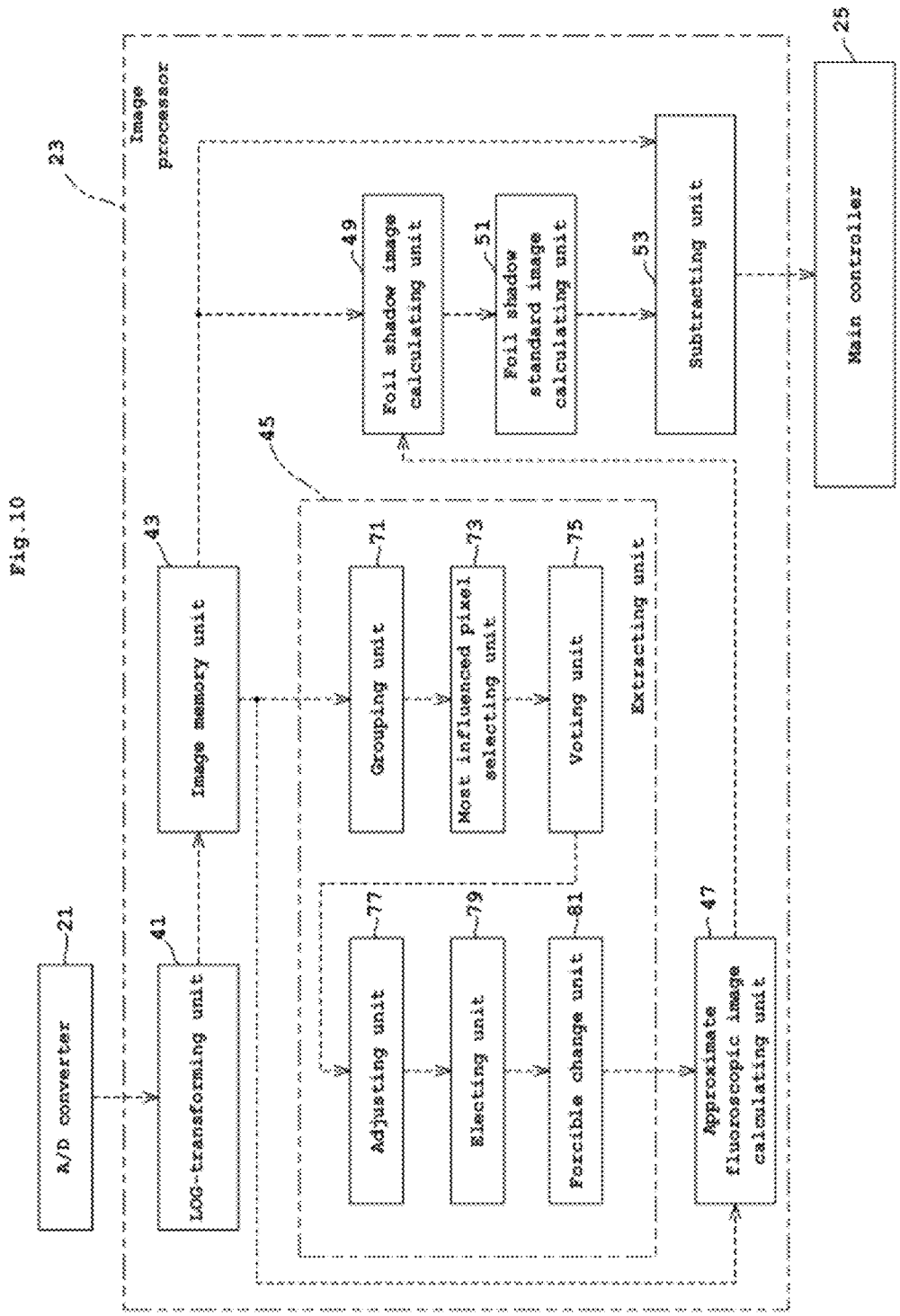
FIG. 10 is a block diagram of an image processor.

Next, reference is made to FIG. 10. FIG. 10 is a block diagram of the image processor.

The image processor 23 receives the digital X-ray detection signals converted by the analog-to-digital converter 21. The image processor 23 includes a LOG-transforming unit 41, an image memory unit 43, an extracting unit 45, an approximate fluoroscopic image calculating unit 47, a foil shadow image calculating unit 49, a foil shadow standard image calculating unit 51 and a subtracting unit 53.

The LOG-transforming unit 41 has a function to LOG-transform the digital X-ray detection signals. This LOG transformation allows arithmetic operations to be carried out by linear sum, which can lighten the load of subsequent arithmetic operations. The image memory unit 43 stores fluoroscopic images based the LOG-transformed X-ray detection signals, and functions also as a buffer. The extracting unit 45 has a function, details of which will be described hereinafter, to extract pixels not influenced by the foil shadows as uninfluenced pixels, based on a fluoroscopic image stored in the image memory unit 43. The approximate fluoroscopic image calculating unit 47 carries out an interpolating process based on the uninfluenced pixels extracted by the extracting unit 45, and calculates an approximate fluoroscopic image having the foil shadows removed from the fluoroscopic image read from the image memory unit 43. The foil shadow image calculating unit 49 calculating a grid foil shadow image which is an image of the grid foil strips 5a by determining a difference between the fluoroscopic image and approximate fluoroscopic image. The foil shadow standard image calculating unit 51 calculates a grid foil shadow standard image by averaging the grid foil shadow image in the longitudinal direction of the grid foil strips 5a. The subtracting unit 53 calculates a foil shadow removed image having the foil shadows removed from the fluoroscopic image by determining a difference between the fluoroscopic image and the grid foil shadow standard image.

The above foil shadow image calculating unit 49 corresponds to the "grid foil shadow image calculating unit" in this invention. The subtracting unit 53 corresponds to the "foil shadow removing unit" in this invention.

Figure 11:
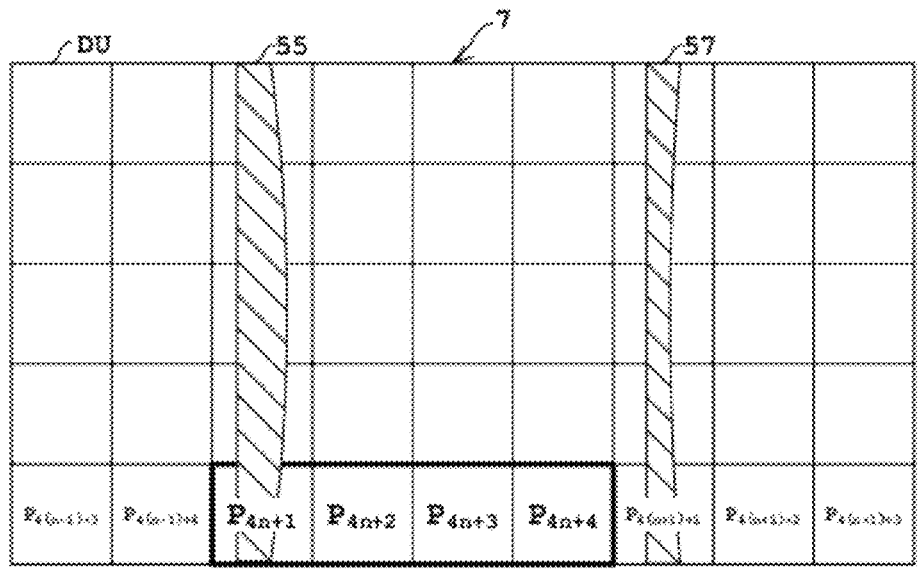
FIG. 11 is a schematic view illustrating a positional relationship between the FPD and grid foil shadows at a time of reference SID.
Figure 12:
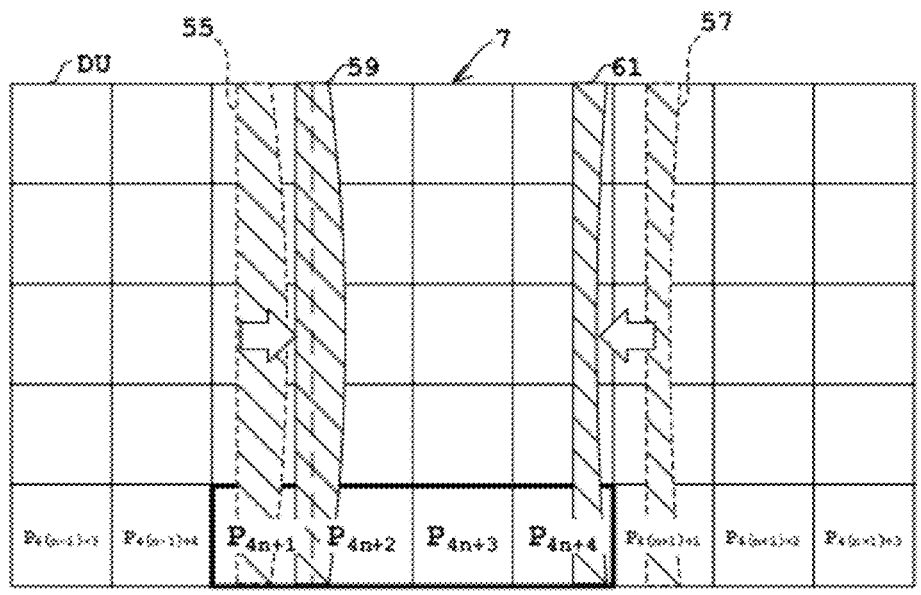
FIG. 12 is a schematic view illustrating a positional relationship between the FPD and grid foil shadows at a time of deviation from the reference SID.

Reference is now made to FIGS. 11 and 12. FIG. 11 is a schematic view illustrating a positional relationship between the FPD and grid foil shadows at a time of reference SID. FIG.

12 is a schematic view illustrating a positional relationship between the FPD and grid foil shadows at a time of deviation from the reference SID.

According to the design adopted here, at the reference SID the foil shadows fall on the X-ray detecting pixels DU of the FPD 7 as shown in FIG. 11, for example. That is, assuming that the X-ray detecting pixels DU of the FPD 7 are set to $P_{4n+1}$ (where n is an integer 0 or more) in the direction of row (transverse direction), the foil shadows fall on the pixels indicated by $P_{4n+1}$ and arranged at intervals of four pixels (or at intervals of three pixels when the three pixels are seen as being skipped). The shape of the grid foil strips 5a is not strictly uniform, and minute shifts will occur with the arrangement of the grid foil strips 3a also. These result in variations in the width (in the direction of row) of the foil shadows as seen in a foil shadow 55 and a foil shadow 57. However, of a group consisting of four pixels ($P_{4n+1}$, $P_{4n+2}$, $P_{4n+3}$ and $P_{4n+4}$), the pixels $P_{4n+2}$, $P_{4n+3}$ and $P_{4n+4}$ forming a group excluding the pixel $P_{4n+1}$ are uninfluenced pixels which are not influenced by the foil shadow 55. Therefore, the foil shadow image calculating unit 49 may carry out an interpolation process using any one of these pixels. However, random quantum noise exists in X-rays, and when uninfluenced pixels are selected based only on the pixel values (X-ray detection signal values), inappropriate pixels can be selected as the uninfluenced pixels.

In the case of a deviation from the reference SID or the C-arm 9 moved as described above, for example, the positions of the foil shadows move from the positions of the foil shadows according to the design value of the reference SID as shown in FIG. 12. For example, a foil shadow 59 appears as straddling the pixel $P_{4n+1}$ and adjoining pixel $P_{4n+2}$ in the group of four pixels ($P_{4n+1}$, $P_{4n+2}$, $P_{4n+3}$ and $P_{4n+4}$). In a different condition, a foil shadow 61 may move completely from pixel $P_{4(n+1)+1}$ onto pixel $P_{4n+4}$. In this way, the pixels not influenced by the foil shadows are changeable also with the position of the C-arm 9, and therefore a contrivance is needed for extracting uninfluenced pixels.

Reference is now made to FIGS. 13 and 14. FIG. 13 is a schematic view showing a relationship between the grid foil shadows and detection values of the pixels in the absence of a patient. FIG. 14 is a schematic view showing a relationship between the grid foil shadows and detection values of the pixels in the presence of a patient.

Figure 13A:
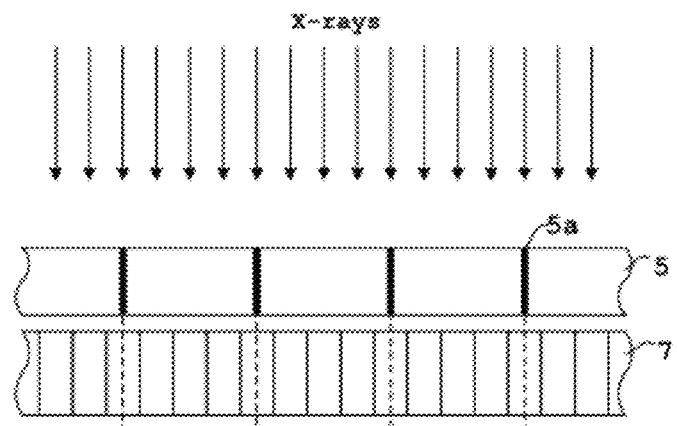
FIG. 13 is a schematic view showing a relationship between the grid foil shadows and detection values of the pixels in the absence of a patient.
Figure 13B:
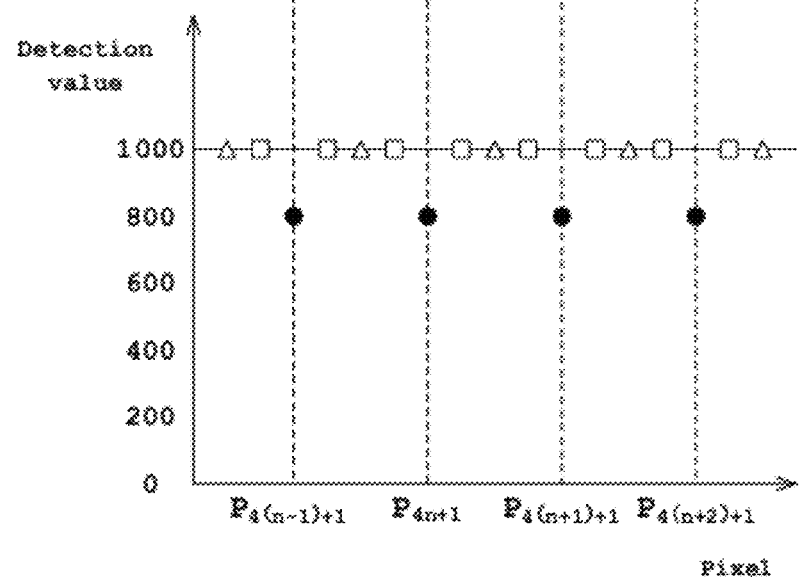

When X-raying is carried out without the patient M placed on the top board 17 as shown in FIG. 13A, X-ray detection signal values will be as follows. As shown in FIG. 13B, the pixels $P_{4n+1}$ with the foil shadows of the grid foil strips 3a falling thereon have X-ray detection signal values (● (black circle) mark) which are reduced about 20% from X-ray detection signal values (Δ (triangle) mark and □ (square) mark) of the other pixels.

Figure 14A:
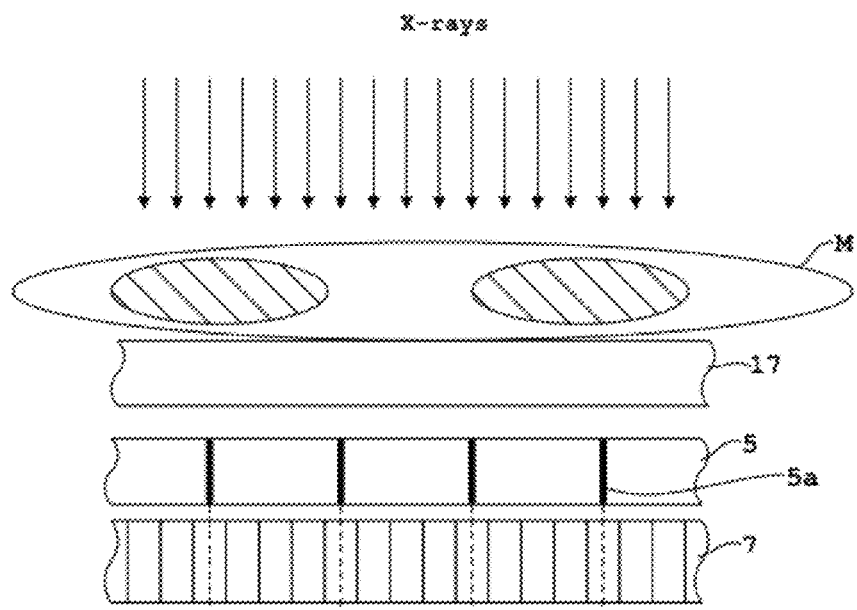
FIG. 14 is a schematic view showing a relationship between the grid foil shadows and detection values of the pixels in the presence of a patient.
Figure 14B:
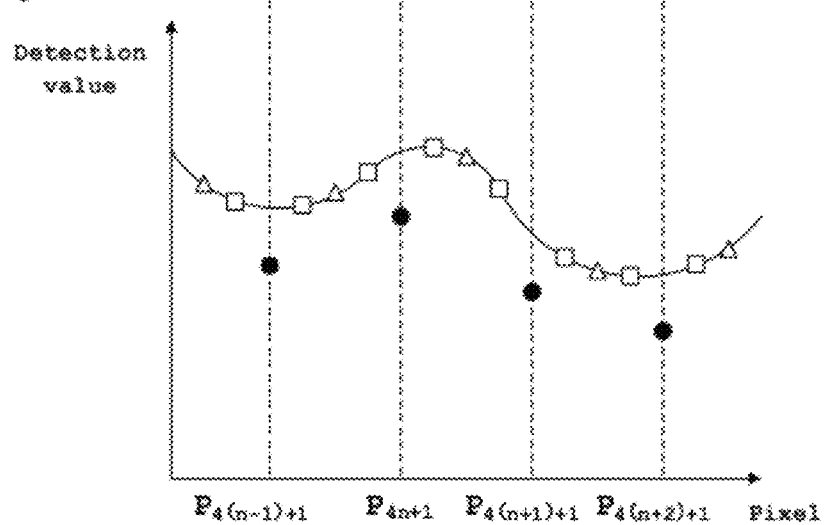

Next, when X-raying is carried out with the patient M placed on the top board 17 as shown in FIG. 14A, X-ray detection signal values will be as follows. As shown in FIG. 14B, the pixels $P_{4n+1}$ with the foil shadows of the grid foil strips 3a falling thereon have X-ray detection signal values (● (black circle) mark) which are lower than X-ray detection signal values (Δ (triangle) mark and □ (square) mark) of the other pixels.

Reference is now made to FIG. 15 showing actual measurements in graphs. FIG. 15 shows an example of detection values of the pixels within one row of the FPD, in which FIG. 15A shows detection values of the entire row, FIG. 15B shows detection values of a middle portion A, and FIG. 15C shows detection values of an end portion B. The FPD 7 used here is 9 inch size with 1440×1440 pixels, the tube voltage is 60 keV, and the elongated SID deviating from the reference SID is 1150 mm.

As shown in FIG. 15A, in pixel numbers 1 to 1440 of the X-ray detecting pixels DU in one row of the FPD 7, there are four locations of turnover in the magnitude relation of the X-ray detection signal values. These locations represent instances of foil shadows straddling the pixels as described hereinbefore. FIG. 15B shows an enlarged graph of the middle portion A of FIG. 15A, in which the foil shadows fall on every fourth pixels, i.e. at regular intervals skipping three pixels. FIG. 15 C shows an enlarged graph of the end portion B of FIG. 15A, which includes an instance of a foil shadow straddling the pixels. It will be seen that the X-ray detection signal values assume a complicated pattern in this graph. Such a complicated pattern formed also indicates a difficulty in extracting uninfluenced pixels.

Reference is made to FIGS. 10 and 16. FIG. 16 is a schematic view showing a voting process. In FIG. 16, the ● (black circle) mark indicates pixels most influenced by the foil shadows, the ○ (white circle) mark indicates pixels not influenced by the foil shadows, and hatched ○ (white circle) mark indicates pixels which are neither of the above two types.

The extraction of uninfluenced pixels noted above is carried out by the extracting unit 45. The extracting unit 45 has a grouping unit 71, a most influenced pixel selecting unit 73, a voting unit 75, an adjusting unit 77, an electing unit 79 and a forcible change unit 81.

The above adjusting unit 77 corresponds to the "first adjusting unit to the fifth adjusting unit" in this invention.

Figure 16A:
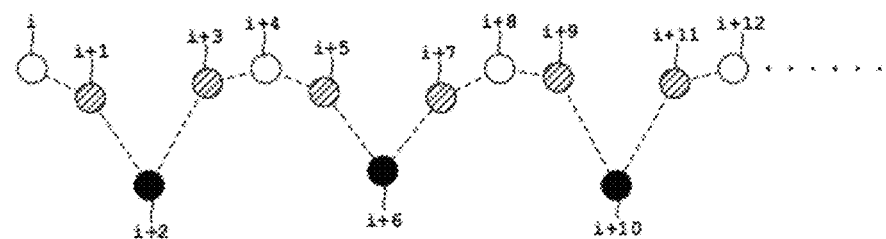
FIG. 16 is a schematic view showing a voting process.
Figure 16B:
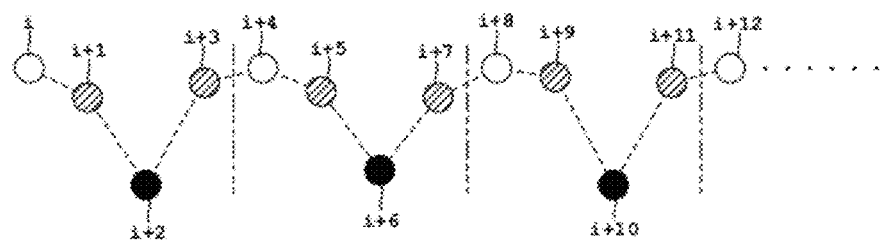

The grouping unit 71 carries out a process of dividing a plurality of pixels i (where i=1 to N) arranged in the direction of row (transverse direction) of the FPD 7 as shown in FIG. 16A, into groups each consisting of a predetermined number of pixels (FIG. 16B). Assume here, for example, that four pixels constitute each group. That is, the grouping unit 71 divides the pixels into a plurality of groups each including four consecutive pixels. In FIG. 16B, the pixels are divided into a group of pixel i, pixel i+1, pixel i+2 and pixel i+3, a group of pixel i+4, pixel i+5, pixel i+6 and pixel i+7, a group of pixel i+8, pixel i+9, pixel i+10 and pixel i+11, a group of pixel i+12 . . . , and so on. The most influenced pixel selecting unit 73 processes each of the groups formed by the grouping unit 71. Specifically, one pixel most influenced by a grid foil shadow 5a in each group is selected as the "most influenced pixel". This is done only by selecting what has an extremely low detection signal value, and is easy compared with finding uninfluenced pixels. Specifically, pixels i+2, i+6 and i+10 in the respective groups will be selected as the most influenced pixels.

Figure 16C:
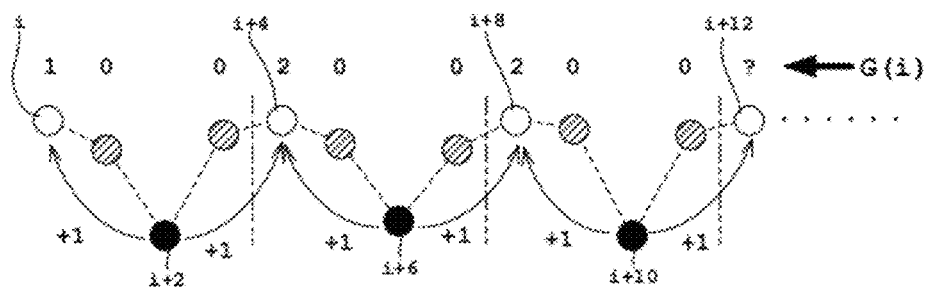

The voting unit 75, based on the positions of the most influenced pixels i+2, i+6 and i+10 in the respective groups selected by the most influenced pixel selecting unit 73, casts a predetermined number votes for pixels i, i+4, i+8 and i+12 which are located next but one to the respective most influenced pixels i+2, i+6 and i+10 forward and backward in the direction of row (FIG. 16C). Here, the predetermined number of votes is set to "1". The electing unit 79, based on the result of voting by the voting unit 75, elects pixels least influenced by the foil shadows as "uninfluenced pixels". Since the number of votes is set to one vote, the votes are cast for pixels next but one forward and backward, and the number of pixels in each group is four, the number of votes G(i) obtained by each pixel i at this time is 0, 1 or 2. The pixels with G(i)=0 are those influenced by the foil shadows, while the pixels of G(i)=2 are those least influenced by the foil shadows. Therefore, the electing unit 79 elects the pixels having obtained the number of votes G(i)=2 as uninfluenced pixels.

Thus, it is so designed that the foil shadows fall on every four pixels, each group is set to every four pixels, and votes are cast for positions spaced from the most influenced pixel in each group by two pixels which are the half of the number of pixels constituting each group, thereby forming peaks of the number of votes at certain places. Moreover, the peaks correspond with a high degree of certainty to positions of the pixels unlikely to be influenced by the foil shadows, and thus the uninfluenced pixels can be elected with a high degree of certainty.

The pixels with G(i)=1 are those for which it is unknown whether they are influenced by the foil shadows or not. So, the adjusting unit 77 carries out the following adjustment for the pixels with G(i)=1.

First, when the number of votes G(i)=2 is obtained by each of pixels next but three to a given pixel forward and backward in the direction of row (i.e. G(i−4)=2 or G(i+4)=2), the number of votes G(i) obtained by this given pixel is adjusted from 1 to 2. This is because four pixels form each group, and so a pixel next but three to a pixel having obtained the number of votes G(i)=2 has a high probability of not being influenced by a foil shadow. Next, when the number of votes G(i)=2 is obtained by a pixel next to a given pixel in the direction of row (i.e. G(i−1)=2 or G(i+1)=2), the number of votes G(i) obtained by this given pixel is adjusted from 1 to 0. This is because the probability of two adjoining pixels not being influenced by a foil shadow or shadows is low. Next, the detection signal values of adjoining pixels among the pixels of G(i)=1 are compared. The number of votes of the pixel with the larger detection signal value is adjusted to 2, and the number of votes of the pixel with the smaller value to 0. This is because, where pixels of G(i)=1 adjoin each other, the pixel with the larger detection signal value is more likely not to be influenced by a foil shadow. Next, when one of pixels next but one to a given pixel forward and backward has two votes (i.e. G(i−2)=2 or G(i+2)=2), the number of votes of this given pixel is adjusted to 0. This is because, when a pixel not influenced by a foil shadow is present close by, the given pixel has a high probability of being influenced by the foil shadow. These operations adjust many pixels with the number of votes G(i)=1 to have the number of votes G(i)=0 or the number of votes G(i)=2, which enables uninfluenced pixels to be extracted within the respective groups.

When there still remain pixels having the number of votes G(i)=1 after the above process, the adjusting unit 77 changes the number of votes of these pixels to G(i)=2. For a group located in an end portion of the FPD 7, the votes are cast only from the group at one side, and there exists a pixel with the number of votes G(i)=1 remaining unchanged. So, this remaining pixel is adjusted to have the number of votes G(i)=2, thereby to extract an uninfluenced pixel from the end portion for use in the interpolation process. Therefore, the interpolation process for the end portions of the FPD 7 can also be carried out with high accuracy.

After the above adjustments are carried out and the uninfluenced pixels are elected by the electing unit 79, the forcible change unit 81 checks whether a forcible changing condition is fulfilled or not, and carries out the following forcible change when the condition is fulfilled.

Even though uninfluenced pixels are extracted through the adjustment described above, there is a possibility of erroneous extraction since, after all, pixels only with a stochastically high degree of certainty are extracted. Under ideal conditions in which no random noise exists, and when an SID used is longer than the reference SID, most of the uninfluenced pixels occurring within one row skip three pixels each. The uninfluenced pixels, skipping two pixels each, occur in only several locations within one row. The uninfluenced pixels, skipping two pixels each, occur substantially equidistantly. Conversely, when the SID used is shorter than the reference SID, most of the uninfluenced pixels occurring within one row skip three pixels each, the uninfluenced pixels, skipping four pixels each, occur in only several locations within one row, and the uninfluenced pixels, skipping four pixels each, occur substantially equidistantly. That is, with whatever SID, the uninfluenced pixels, skipping two pixels each, and the uninfluenced pixels, skipping four pixels each, never occur at the same time. So, a high probability of erroneous extraction is assumed when the forcible change unit 81 finds fulfillment of a "forcible changing condition" that a predetermined range (e.g. a range of five uninfluenced pixels) includes an uninfluenced pixel skipping four pixels, and an uninfluenced pixel skipping two pixels. Then, the uninfluenced pixels are forcibly changed so that each have three pixels at both sides. This can inhibit lowering of the accuracy of an approximate fluoroscopic image due to the erroneous extraction.

Figure 17:
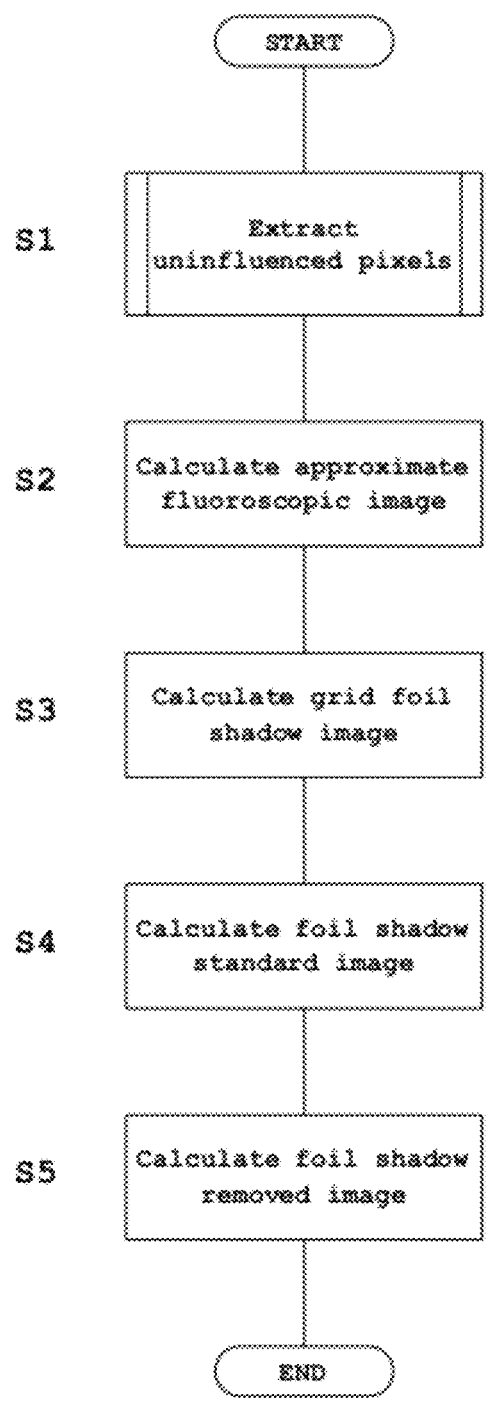
FIG. 17 is a flow chart showing operation of the image processor.

Next, a process of X-ray fluoroscopic imaging carried out by the above X-ray apparatus 1 will be described with reference to FIGS. 17 and 18. FIG. 17 is a flow chart showing operation of the image processor. FIG. 18 is a flow chart showing a process of extracting uninfluenced pixels.

First, X-ray fluoroscopic imaging carried out before the processes in the flow chart will be described. The radiographer sets an amount of the SID, an amount of movement of the C-arm 9, a tube voltage and a tube current to the input unit 27. The main controller 25 outputs the set amount of the SID and amount of movement of the C-arm 9 to the C-arm movement controller 15. The C-arm movement controller 15 controls the C-arm moving mechanism 13 to move the C-arm 9. The main controller 25 also outputs instructions to the X-ray tube controller 19 to control the X-ray tube 3 with the set tube voltage and tube current. Next, when the radiographer instructs a start of X-raying from the input unit 27, the main controller 25 controls the X-ray tube controller 19 and FPD 7. The X-ray tube controller 19 applies the tube voltage and tube current to the X-ray tube 3 based on the instructions from the main controller 25. Then, X-rays are emitted from the X-ray tube 3 to the patient M. X-rays transmitted through the patient M, while scattered X-rays are inhibited by the synchronous grid 5, fall on the FPD 5 to be detected by the X-ray detecting pixels DU. X-ray detection signals generated by the X-ray detecting pixels DU are outputted to the image processor 23 to be LOG-transformed by the LOG-transforming unit 41. The LOG-transformed X-ray detection signals are stored as a fluoroscopic image in the image memory unit 43.

Step S1

The extracting unit 45 carries out a process of extracting uninfluenced pixels. Specifically, this process follows the flow chart shown in FIG. 18.

Step T1

The grouping unit 71 divides all the pixels in one row into groups as described above. This grouping is carried out for all the rows of the FPD 7.

Step T2

The most influenced pixel selecting unit 73 selects a pixel most influenced by the foil shadows in each group as described above.

Step T3

The voting unit 75 casts votes in the procedure described above for fore and aft pixels spaced from the most influenced pixels.

Step T4

The adjusting unit 77 adjusts the number of votes obtained by the pixels whose vote is one, as described above.

Step T5

Based on the result of voting for each pixel, the electing unit 79 elects uninfluenced pixels as described above.

Steps T6 and T7

Figure 19A:
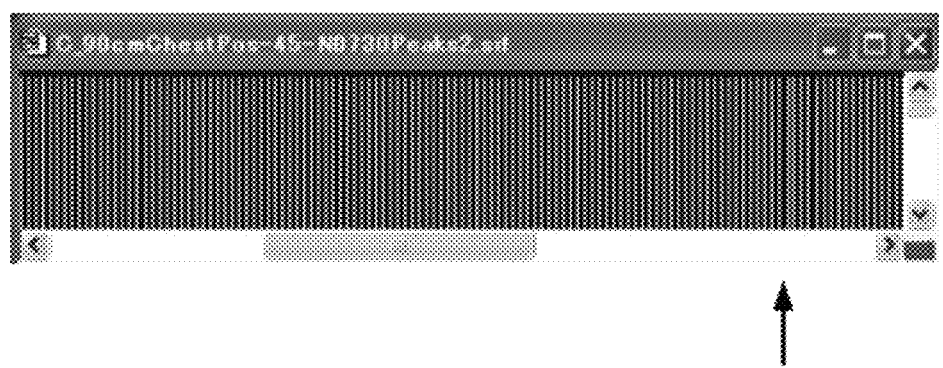
FIG. 19A shows a case of selecting improper uninfluenced pixels.
Figure 19B:
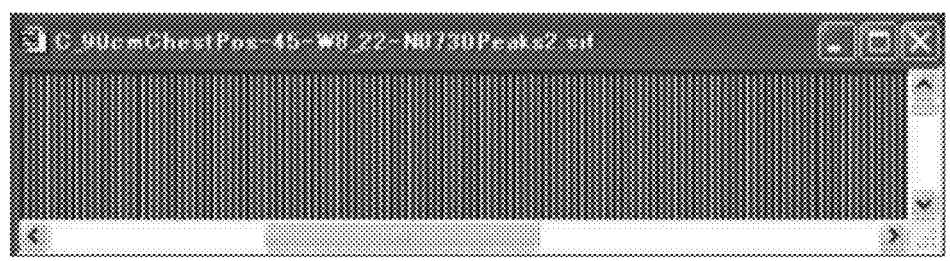
FIG. 19B shows a state after a forceful changing process.

The forcible change unit 81 checks whether the forcible changing condition which may take place rarely is fulfilled, and forcibly changes the numbers of votes according to a result. Reference is made to FIG. 19 for a specific example. FIG. 19 includes schematic views showing uninfluenced pixels after the extracting process, in which FIG. 19A shows a case of selecting inappropriate uninfluenced pixels, and FIG. 19B shows a state after a forceful changing process. In these figures, the white lines represent the uninfluenced pixels elected in step T5, and the black lines represent pixels other than the uninfluenced pixels and including the most influenced pixels.

FIG. 19A shows a case of the above forcible changing condition being fulfilled. Specifically, in two locations near the right end as indicated by an arrow in FIG. 19A, an uninfluenced pixel is elected skipping four pixels and an uninfluenced pixel is elected skipping two pixels. When such elections are made, a forcible change is carried out in steps T6 and T7. The result is shown in FIG. 19B. In this figure, the forcible change has been carried out to show that pixels skipping three pixels are elected as uninfluenced pixels.

Step T1 described above corresponds to the "grouping step" in this invention. Step T2 corresponds to the "most influenced pixel selecting step". Step T3 corresponds to the "voting step". Step T4 corresponds to the "adjusting step". Step T5 corresponds to the "electing step". Step T4 corresponds also to the "first to fifth adjusting steps". Steps T6 and T7 correspond to the "forcible changing step".

Reference is made to the flow chart of FIG. 17 again.

Step S2

The approximate fluoroscopic image calculating unit 47 calculates, by interpolation process, detection signal values corresponding to positions of the most influenced pixels, based on the uninfluenced pixels outputted from the extracting unit 45. Then, an approximate fluoroscopic image is calculated based on the fluoroscopic image from the image memory unit 4 and results of the interpolation. The interpolation process may employ cubic interpolation such as cubic spline method, for example.

Step S3

The foil shadow image calculating unit 49 calculates a grid foil shadow image showing only the foil shadows, by determining a difference between the fluoroscopic image from the image memory unit 43 and the approximate fluoroscopic image from the approximate fluoroscopic image calculating unit 47.

Step S4

The foil shadow standard image calculating unit 51 calculates a grid foil shadow standard image by averaging the grid foil shadow image from the foil shadow image calculating unit 49, piecewise by units of several tens of pixels in the longitudinal direction corresponding to the direction of length of the grid foil strips 5a. That is, correction is made by averaging variations in the foil shadows due to random errors such as quantum noise and the like as shown in FIGS. 11 and 12. The entire length of each grid foil strip 5a corresponds to 1000 to 2000 pixels. By averaging these piecewise, interpolation errors included in the grid foil shadow image are removed therefrom, while leaving distortions of the foil itself in the image.

Step S5

The subtracting unit 53 calculates a foil shadow removed fluoroscopic image by determining a difference between the fluoroscopic image from the image memory unit 43 and the grid foil shadow standard image from the foil shadow standard image calculating unit 51. By removing the standardized foil shadows from the fluoroscopic image, an X-ray fluoroscopic image of the patient from which the interpolation errors have been removed can be obtained.

The X-ray fluoroscopic image of the patient obtained in this way is displayed on the monitor 29 or stored in the storage unit 31 through the main controller 25.

Step S1 described above corresponds to the "extracting step" in this invention. Step S2 corresponds to the "approximate fluoroscopic image calculating step". Step S3 corresponds to the "grid foil shadow image calculating step". Step S4 corresponds to the "foil shadow standard image calculating step". Step S5 corresponds to the "foil shadow removing step".

Next, reference is made to FIGS. 20 and 21. FIG. 20 includes views showing a process according to this invention, in which FIG. 20A shows a foil shadow removed image, and FIG. 20B shows selected uninfluenced pixels. FIG. 21 includes views showing a process according to a proposed example, in which FIG. 21A shows a foil shadow removed image, and FIG. 21B shows selected uninfluenced pixels.

In this invention, as shown in FIG. 20B, uninfluenced pixels are extracted at substantially equal intervals. As a result, as shown in FIG. 20A, an X-ray fluoroscopic image which is a foil shadow removed image is free from artifacts.

On the other hand, in the proposed example, as shown in FIG. 21B, uninfluenced pixels are extracted at irregular intervals. As a result, as shown in FIG. 21A, an X-ray fluoroscopic image obtained has artifacts remaining thereon (encircled area in the figure) under the influence of foil shadows.

This invention is not limited to the foregoing embodiment, but may be modified as follows:

(1) In the foregoing embodiment, the construction provides one grid foil strip 5a for every four pixels, but this invention is not limited to this. For example, one grid foil strip 5a may be provided for every eight pixels. In this case, the grouping described hereinbefore may be carried out for every eight pixels, with votes cast for fourth pixels forward and backward.

(2) In the foregoing embodiment, for the pixels given one vote and remaining to the last, the number of votes obtained is changed to 2. Such process may be omitted when peripheral portions of the X-ray fluoroscopic image are not processed. This can lighten the load on the process.

(3) In the foregoing embodiment, checking is made whether the forcible changing condition is fulfilled. When the frequency of occurrence is low, such checking process may be omitted. This can lighten processing load, and increase processing speed.

(4) In the foregoing embodiment, the X-ray detection signals are LOG-transformed by the LOG-transforming unit 41. It is not necessary to provide the LOG-transforming unit 41 where the arithmetic capability has leeway. This can simplify the construction, and reduce apparatus cost.

This invention may be embodied in other specific forms without departing from the spirit or essential attributes thereof and, accordingly, reference should be made to the appended claims, rather than to the foregoing specification, as indicating the scope of the invention.

What is claimed is:

1. A grid foil shadow removing method for a radiographic apparatus for obtaining fluoroscopic images and having a synchronous grid with grid foil strips arranged at regular intervals so that grid foil shadows fall on middles of pixels which detect radiation, the method comprising:

- an extracting step including a grouping step for dividing pixels forming a fluoroscopic image into groups each having a predetermined number of pixels within each row in a direction of row, a most influenced pixel selecting step for selecting a pixel most influenced by one of the grid foil shadows in each group as most influenced pixel, a voting step for casting, with the most influenced pixel in each group serving as a reference, a predetermined number of votes for other pixels spaced apart forward and backward in the direction of row, and an electing step for electing a pixel given a maximum number of votes within each group as an uninfluenced pixel which is free from influences of a foil shadow of the grid;
- an approximate fluoroscopic image calculating step for obtaining an approximate fluoroscopic image by carrying out an interpolation process based on detection signal values of the uninfluenced pixels;
- a grid foil shadow image calculating step for obtaining a grid foil shadow image based on a difference between the fluoroscopic image and the approximate fluoroscopic image;
- a foil shadow standard image calculating step for obtaining a foil shadow standard image by averaging the grid foil shadow image in a longitudinal direction of the grid foil shadows; and
- a foil shadow removing step for removing the grid foil shadows from the fluoroscopic image based on a difference between the fluoroscopic image and the foil shadow standard image, thereby to obtain a foil shadow removed image.

2. The method according to claim 1, wherein:
- when the predetermined number of pixels constituting each group is four, and the predetermined number of votes is 1;
- the voting step casts 1 vote for each of a pixel located next but one forward and a pixel located next but one backward in the direction of row; and
- the electing step elects a pixel having obtained 2 votes as the uninfluenced pixel;
- the voting step and the electing step having, interposed therebetween adjusting steps including:
- a first adjusting step for adjusting the number of votes obtained to 2 for a pixel whose number of votes obtained is 1 when pixels located next but three to such pixel forward and backward in the direction of row have 2 votes, respectively;
- a second adjusting step for adjusting the number of votes obtained to 0 for a pixel whose number of votes obtained is 1 when a pixel located next to such pixel in the direction of row has 2 votes;
- a third adjusting step for comparing detection signal values of a pixel whose number of votes obtained is 1 and an adjoining pixel, adjusting the number of votes from 1 to 2 for the pixel having the larger detection signal value, and adjusting the number of votes to 0 for the pixel having the smaller detection signal value; and
- a fourth adjusting step for adjusting the number of votes obtained from 1 to 0 for a pixel whose number of votes obtained is 1 when one of pixels located next but one to such pixel forward and backward in the direction of row has 2 votes.

3. The method according to claim 2, further comprising a fifth adjusting step executed, when there remains a pixel whose number of votes obtained is 1 after the fourth adjusting step, for adjusting the number of votes obtained by such pixel to 2.

4. The method according to claim 2, comprising a forcible changing step executed after the extracting step, when a predetermined range includes an uninfluenced pixel skipping four pixels, and an uninfluenced pixel skipping two pixels, for forcibly changing the uninfluenced pixels so that each have three pixels at both sides.

5. The method according to claim 3, comprising a forcible changing step executed after the extracting step, when a predetermined range includes an uninfluenced pixel skipping four pixels, and an uninfluenced pixel skipping two pixels, for forcibly changing the uninfluenced pixels so that each have three pixels at both sides.

6. The method according to claim 1, wherein the most influenced pixel selecting step is executed for selecting a pixel having a minimum detection signal value as the most influenced pixel.

7. The method according to claim 2, wherein the most influenced pixel selecting step is executed for selecting a pixel having a minimum detection signal value as the most influenced pixel.

8. The method according to claim 3, wherein the most influenced pixel selecting step is executed for selecting a pixel having a minimum detection signal value as the most influenced pixel.

9. The method according to claim 4, wherein the most influenced pixel selecting step is executed for selecting a pixel having a minimum detection signal value as the most influenced pixel.

10. The method according to claim 5, wherein the most influenced pixel selecting step is executed for selecting a pixel having a minimum detection signal value as the most influenced pixel.

11. A radiographic apparatus for obtaining radiographs, comprising:
- a radiation emitting device for emitting radiation to a patient;
- a radiation detector having pixels arranged in a two-dimensional array for detecting radiation transmitted through the patient;
- a synchronous grid with foil strips arranged at regular intervals so that grid foil shadows fall on middles of the pixels of the radiation detector;
- an extracting unit including a grouping unit for dividing pixels forming a fluoroscopic image into groups each having a predetermined number of pixels within each row in a direction of row, a most influenced pixel selecting unit for selecting a pixel most influenced by one of the grid foil shadows in each group as most influenced pixel, a voting unit for casting, with the most influenced pixel in each group serving as a reference, a predetermined number of votes for other pixels spaced apart forward and backward in the direction of row, and an electing unit for electing a pixel given a maximum number of votes within each group as an uninfluenced pixel which is free from influences of a foil shadow of the grid;
- an approximate fluoroscopic image calculating unit for obtaining an approximate fluoroscopic image by carrying out an interpolation process based on detection signal values of the uninfluenced pixels;
- a grid foil shadow image calculating unit for obtaining a grid foil shadow image based on a difference between the fluoroscopic image and the approximate fluoroscopic image;

a foil shadow standard image calculating unit for obtaining a foil shadow standard image by averaging the grid foil shadow image in a longitudinal direction of the grid foil shadows; and a foil shadow removing unit for removing the grid foil shadows from the fluoroscopic image based on a difference between the fluoroscopic image and the foil shadow standard image, thereby to obtain a foil shadow removed image.

12. The apparatus according to claim 11, wherein:

when the predetermined number of pixels constituting each group is four, and the predetermined number of votes is 1;

the voting unit casts 1 vote for each of a pixel located next but one forward and a pixel located next but one backward in the direction of row; and the electing unit elects a pixel having obtained 2 votes as the uninfluenced pixel;

the voting unit and the electing unit having, interposed therebetween, an adjusting unit including:

a first adjusting unit for adjusting the number of votes obtained from 1 to 2 for a pixel whose number of votes obtained is 1 when pixels located next but three to such pixel forward and backward in the direction of row have 2 votes, respectively;

a second adjusting unit for adjusting the number of votes obtained to 0 for a pixel whose number of votes obtained is 1 when a pixel located next to such pixel in the direction of row has 2 votes;

a third adjusting unit for comparing detection signal values of a pixel whose number of votes obtained is 1 and an adjoining pixel, adjusting the number of votes from 1 to 2 for the pixel having the larger detection signal value, and adjusting the number of votes from 1 to 0 for the pixel having the smaller detection signal value; and a fourth adjusting unit for adjusting the number of votes obtained from 1 to 0 for a pixel whose number of votes obtained is 1 when one of pixels located next but one to such pixel forward and backward in the direction of row has 2 votes.

13. The apparatus according to claim 12, wherein the adjusting unit further includes a fifth adjusting unit arranged, when there remains a pixel whose number of votes obtained is 1 after the adjustment by the fourth adjusting unit, to adjust the number of votes obtained by such pixel to 2.

14. The apparatus according to claim 12, further comprising a forcible changing unit arranged, after the process by the extracting unit, when a predetermined range includes an uninfluenced pixel skipping four pixels, and an uninfluenced pixel skipping two pixels, to forcibly change the uninfluenced pixels so that each have three pixels at both sides.

15. The apparatus according to claim 13, comprising a forcible changing unit arranged, after the process by the extracting unit, when a predetermined range includes an uninfluenced pixel skipping four pixels, and an uninfluenced pixel skipping two pixels, to forcibly change the uninfluenced pixels so that each have three pixels at both sides.

16. The apparatus according to claim 11, wherein the most influenced pixel selecting unit is arranged to select a pixel having a minimum detection signal value as the most influenced pixel.

17. The apparatus according to claim 12, wherein the most influenced pixel selecting unit is arranged to select a pixel having a minimum detection signal value as the most influenced pixel.

18. The apparatus according to claim 13, wherein the most influenced pixel selecting unit is arranged to select a pixel having a minimum detection signal value as the most influenced pixel.

19. The apparatus according to claim 14, wherein the most influenced pixel selecting unit is arranged to select a pixel having a minimum detection signal value as the most influenced pixel.

20. The apparatus according to claim 15, wherein the most influenced pixel selecting unit is arranged to select a pixel having a minimum detection signal value as the most influenced pixel.

* * * * *